(12) United States Patent
Jefferson et al.

(10) Patent No.: US 7,432,264 B2
(45) Date of Patent: Oct. 7, 2008

(54) ANTIMICROBIAL BIARYL COMPOUNDS

(75) Inventors: Elizabeth Anne Jefferson, La Jolla, CA (US); Eric E. Swayze, Carlsbad, CA (US); Punit P. Seth, San Marcos, CA (US); Dale E. Robinson, Jr., San Marcos, CA (US)

(73) Assignee: Isis Pharmaceuticals, Inc., Carlsbad, CA (US)

( * ) Notice: Subject to any disclaimer, the term of this patent is extended or adjusted under 35 U.S.C. 154(b) by 361 days.

(21) Appl. No.: 10/914,256

(22) Filed: Aug. 9, 2004

(65) Prior Publication Data

US 2005/0032805 A1    Feb. 10, 2005

Related U.S. Application Data

(63) Continuation-in-part of application No. 09/630,122, filed on Aug. 1, 2000, now Pat. No. 6,849,660.

(51) Int. Cl.
| | |
|---|---|
| A61P 31/04 | (2006.01) |
| A61K 31/495 | (2006.01) |
| A61K 31/497 | (2006.01) |
| A61K 31/50 | (2006.01) |
| C07D 241/02 | (2006.01) |
| C07D 241/36 | (2006.01) |
| C07D 401/00 | (2006.01) |
| C07D 405/00 | (2006.01) |
| C07D 409/00 | (2006.01) |
| C07D 411/00 | (2006.01) |
| C07D 413/00 | (2006.01) |
| C07D 417/00 | (2006.01) |
| C07D 419/00 | (2006.01) |

(52) U.S. Cl. .............. 514/249; 514/252.11; 514/252.13; 514/253.06; 514/253.11; 514/254.01; 514/254.03; 544/353; 544/354; 544/357; 544/363; 544/364; 544/367; 544/379

(58) Field of Classification Search ................. 514/249, 514/252.11, 252.13, 253.06, 253.11, 254.01, 514/254.03; 544/353, 354, 357, 363, 364, 544/367, 379
See application file for complete search history.

(56) References Cited

FOREIGN PATENT DOCUMENTS

| WO | WO96/10559 | 4/1996 |
|---|---|---|
| WO | WO 02/09648 A2 * | 2/2002 |

OTHER PUBLICATIONS

Swayze et al., SAR by MS: A Ligand Based Technique for Drug Lead Discovery Against Structured RNA Targets, Journal of Medicinal Chemistry, vol. 45, No. 18, pp. 3816-3819, Aug. 29, 2002.*
Muller, et al., "Polyamide oligomers from epsilon-aminocaproic acid and isomeric aminophenylcarboxylic acids," J. Praktische Chemie (1970) 312:78-89.
Ehmer, et al., "Development of a simple and rapid assay for the evaluation of inhibitors of human 17 alpha-hydroxylase-C17,20 lyase (P450c17), by coexpression of P450c17 with NADPH-cytochrome-P450-reductase in *Escherichia coli*," J. Steroid Biochem. Mol. Biol. (2000) 75:57-63.
Gravel, et al., "Resin-to-resin Suzuki coupling of solid supported arylboronic acids," J. Combinatorial Chem. (2000) 2:228-231.
Marchbanks, et al., "New fluoroquinolones," Hospital Ther. (1988) 7:18-35.
Parry, "Pharmacology and clinical uses of quinolne antibiotics," Medical Times (1988) 116:19, 39-45.
Percival, A., (ed.), "Quinolines—their future in clinical practice," Royal Soc. Med. Services (1986).
Shah, "Quinolones," Prog. Drug, Res. (1987) 31:243-256.
Lehninger, Principles of Biochemistry, Worth, NY, 1985.
Davis, (ed.) Amino Acids and Peptides, Chapman and Hall, NY, 1985.

* cited by examiner

*Primary Examiner*—Brenda L Coleman

(57) ABSTRACT

Provided are antibacterial biaryl compounds having micromolar MIC activity against Gram-negative and Gram-positive pathogens, including a methicillin-resistant *S. aureus* strain.

10 Claims, No Drawings

ANTIMICROBIAL BIARYL COMPOUNDS

CROSS-REFERENCE TO RELATED APPLICATION

This application is a continuation-in-part of U.S. patent application Ser. No. 09/630,122 filed Aug. 1, 2000, now U.S. Pat. No. 6,849,660, which is hereby incorporated by reference in its entirety.

STATE REGARDING FEDERALLY SPONSORED RESEARCH

This work reported herein was supported in part by the National Institute for Health (NIH) (SBIR grant R44 AI45210-03) and was made with United States Government Support under DARPA contract N65236-99-1-5419. The United States Government may have certain rights in the invention.

FIELD OF THE INVENTION

The present invention relates to novel biaryl compounds useful as therapeutic agents, and in particular to biphenyl compounds and related analogs having antimicrobial activity.

BACKGROUND OF THE INVENTION

In recent years, the emergence and spread of multi-drug resistant pathogens have become a serious problem in treating infectious disease. See Livermore, D. Nature Reviews Microbiology 2004, 2, 73-78; Tenover, F. C. Pharmacy world & science, Sep. 22, 1995, 17, 149-151. As a result of this urgent health concern, there is a need to identify new antibiotics with unexploited modes of action.

The chemical and medical literature describes a myriad of compounds that are said to be antimicrobial, i.e., capable of destroying or suppressing the growth or reproduction of microorganisms, such as bacteria. In particular, antibacterials include a large variety of naturally-occurring (antibiotic), synthetic, or semi-synthetic compounds. They may be classified as aminoglycosides, ansamacrolides, beta-lactams (including penicillins and cephalosporins), lincosaminides, macrolides, nitrofurans, nucleosides, oligosaccharides, peptides and polypeptides, phenazines, polyenes, polyethers, quinolones, tetracyclines, and sulfonamides. Such antibacterials and other antimicrobials are described in Antibiotics, Chemotherapeutics, and Antibacterial Agents for Disease Control (M. Grayson, editor, 1982), and E. Gale et al., The Molecular Basis of Antibiotic Action 2d Edition (1981).

The mechanisms of action of these antibacterials vary. However they can generally be classified as functioning in one of the following ways. Antibacterials may function by inhibiting cell wall synthesis or repair; by altering cell wall permeability; by inhibiting protein synthesis; or by inhibiting synthesis of nucleic acids. For example, beta-lactam antibacterials act through inhibiting the essential penicillin binding proteins (PBPs) in bacteria, which are responsible for cell wall synthesis. On the other hand, quinolones act by inhibiting synthesis of bacterial DNA, thus preventing the bacteria from replicating.

Not surprisingly, the pharmacological characteristics of antibacterials and other antimicrobials, as well as their suitability for a specific clinical use, varies considerably. For example, the classes of antimicrobials (and members within a class) may vary in their relative efficacy against different types of microorganisms and their susceptibility to development of microbial resistance. These antimicrobials may also differ in their pharmacological characteristics, such as their bioavailability, and biodistribution. Accordingly, selection of an appropriate antibacterial (or other antimicrobial) in any given clinical situation can be a complicated analysis of many factors, including the type of organism involved, the desired method of administration, and the location of the infection to be treated.

The pharmaceutical literature is replete with attempts to develop improved antimicrobials (i.e., compounds that have a broader scope of activity, greater potency, improved pharmacology, and/or less susceptibility to resistance development.) One group of antimicrobials recently developed for clinical use is the quinolones. These compounds include, for example, nalidixic acid, difloxacin, enoxacin, fleroxacin, norfloxacin, lomefloxacin, ofloxacin, ciprofloxacin, and pefloxacin. See, C. Marchbanks and M. Dudley, "New Fluoroquinolones,@ 7 Hospital Therapy 18 (1988); P. Shah, "Quinolones,@ 31 Prog. Drug Res. 243 (1987); Quinolones—Their Future in Clinical Practice, (A. Percival, Editor, Royal Society of Medical Services, 1986); and M. Parry, "Pharmacology and Clinical Uses of Quinolone Antibiotics,@ 116 Medical Times 39 (1988).

However, many such attempts to produce improved antimicrobials have produced equivocal results. For example, the quinolones often show reduced effectiveness against certain clinically important pathogens, such as gram positive bacteria and/or anaerobic bacteria. The quinolones also have limited water solubility limiting their bioavailability and suitability for parenteral dosing. They may also produce adverse side effects, such as gastrointestinal disturbance and central nervous system effects such as convulsions. Accordingly there remains a need for new effective antimicrobial compounds.

SUMMARY OF THE INVENTION

According to an aspect of the present invention there is provided compounds

In some embodiments, the invention is a compound having the formula:

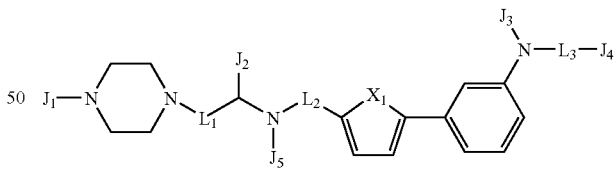

wherein $X_1$ is $CH_2$, O, S or NH;

each $L_1$, $L_2$ and $L_3$ is, independently, $CR_1R_2$, C=O or S(=O)(=O);

each $R_1$ and $R_2$ is, independently, H or $C_1$-$C_6$ alkyl;

$J_1$ is or H, $C_1$-$C_8$ alkyl; C(=O)O-alkyl or S(=O)(=O)-alkyl;

$J_2$ is —$(CH_2)_n$—$NR_3R_4$ or -p-$C_6H_4$—O—$(CH_2)_n$—$NR_3R_4$;

each $R_3$ and $R_4$ is, independently, H or $C_1$-$C_6$ alkyl;

each $J_3$ and $J_5$ is, independently, H or $C_1$-$C_6$ alkyl;

$J_4$ has one of the formulas:

[structures shown: substituted phenyl/pyridyl with $(-A_1)_m$; naphthyl with $(-A_1)_m$; biphenyl with $(-A_1)_m$ and $(-A_2)_{mm}$; quinoxaline-2,3-dione; 1,2,3,4-tetrahydroquinoxaline with CH$_3$ groups; naphthyl/quinoline with $(-A_1)_m$]

or

[1,3,4-thiadiazole structure]

wherein:

each Z is, independently, CH or N;

each $A_1$ and $A_2$ is, independently, halogen, hydroxyl, amino, $C_1$-$C_6$ alkyl, $C_2$-$C_6$ alkenyl, $C_2$-$C_6$ alkynyl or alkoxy;

n is from 1 to about 6;

m is 0, 1, 2, 3 or 4; and mm is 0, 1, 2, 3, 4 or 5.

In some preferred embodiments, $X_1$ is O.

In other embodiments, $L_1$ is C=O or S(=O)(=O).

In still others, $X_1$ is O and $L_1$ is C=O.

In yet other embodiments of the invention, $R_1$ and $R_2$ are H.

In another embodiment, $J_1$ is H.

In another embodiment, $J_2$ is -p-$C_6H_4$—O—$(CH_2)_n$—$NR_3R_4$.

In other embodiments, $R_3$ and $R_4$ are each $C_1$-$C_6$ alkyl, in some embodiments, preferably $R_3$ and $R_4$ are each $CH_3$.

In other embodiments, $J_4$ has one of the formulas:

[structures shown: 2-iodophenyl; 3,4-dichlorophenyl; 4-bromophenyl; 6-bromo-2-naphthyl; 4-chloro-2-methylquinolin-6-yl; quinolin-6-yl; 2-naphthyl]

-continued

[structures shown: 4-chloro-3-ethyl-2-methylquinolin-6-yl; 4-biphenyl]

some preferred embodiments where $J_4$ is one of these formulas, $L_1$ is C(=O). In other embodiments, $L_1$ is C(=O) and $J_2$ is -p-$C_6H_4$—O—$(CH_2)_n$—$NR_3R_4$. In yet another embodiment, $L_1$ is C(=O), $J_2$ is -p-$C_6H_4$—O—$(CH_2)_n$—$NR_3R_4$, and $R_3$ and $R_4$ are each $CH_3$.

In certain preferred embodiments, compounds of the invention have the formula:

[complex structure shown with piperazine, furan, and substituted aryl groups, labeled $J_6$, $J_7$, $J_8$, $J_9$]

wherein $J_6$ is or H or $C_1$-$C_8$ alkyl;

$J_8$ has one of the formulas:

[structures shown: 4-bromophenyl; 6-bromo-2-naphthyl; 2-naphthyl; 4-chloro-3-ethyl-2-methylquinolin-6-yl; 4-biphenyl]

each $J_7$ and $J_9$ is, independently, H or $C_1$-$C_6$ alkyl.

Other embodiments of invention are methods of treating bacterial infection in a mammal by administering to the mammal an effective amount of a compound described herein.

In a preferred embodiment the mammal to be treated is a human.

In some embodiments, the bacteria behind the bacterial infection is at least one of *Streptococcus pyogenes, Enterococcus faecalis, Escherichia coli, Klebsiella pneumoniae* or *Staphylococcus aureus.*

In another aspect of the invention there is provided a method of treating bacterial infection in a mammal comprising administering to said mammal an effective amount of a biaryl compound of the invention.

These and other aspects of the invention will be apparent to those skilled in the art upon reading this specification.

DETAILED DESCRIPTION OF THE INVENTION

Compounds, developed from the basic biaryl compounds of related U.S. patent application Ser. No. 09/630,122, are provided having therapeutic activity, in particular antibacterial activity, having the general formula (I):

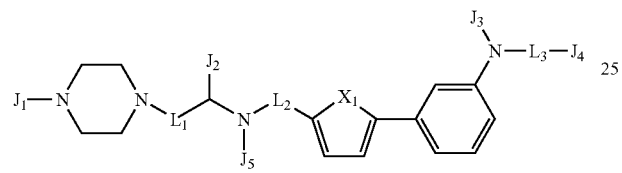

According to the present invention, $X_1$ is $CH_2$, O, S or NH. In some preferred embodiments, $X_1$ is O.

Each $L_1$, $L_2$ and $L_3$ is, independently, $CR_1R_2$, C=O or S(=O)(=O). In some preferred embodiments, $L_1$ is C=O or S(=O)(=O). In some preferred embodiments, $X_1$ is O and $L_1$ is C=O.

$R_1$ and $R_2$ is, independently, H or $C_1$-$C_6$ alkyl. Preferably, $R_1$ and $R_2$ are H.

$J_1$ is H, $C_1$-$C_8$ alkyl; C(=O)O-alkyl or S(=O)(=O)-alkyl. In some preferred embodiments, $J_1$ is H.

$J_2$ is —$(CH_2)_n$—$NR_3R_4$ or -p-$C_6H_4$—O—$(CH_2)_n$—$NR_3R_4$. Preferably, $J_2$ is -p-$C_6H_4$—O—$(CH_2)_n$—$NR_3R_4$.

Each $R_3$ and $R_4$ is, independently, H or $C_1$-$C_6$ alkyl. In some embodiments, $R_3$ and $R_4$ are each $C_1$-$C_6$ alkyl, preferably $R_3$ and $R_4$ are each $CH_3$.

Each $J_3$ and $J_5$ is, independently, H or $C_1$-$C_6$ alkyl.

$J_4$ is a single or multiple ring system comprising one or more substituted or unsubstituted aromatic and/or heterocyclic rings that can be present alone, fused or linked together to form a variety of different ring configurations. The heterocyclic rings can be unsaturated, saturated or at some state between e.g. partially saturated. Substituent groups can be present at any available site in each of the rings present. Preferred substituent groups include hydroxyl, amino, alkoxy, carboxy, benzyl, phenyl, nitro, thiol, thioalkoxy, halogen, alkyl, aryl, alkenyl and alkynyl. $J_4$ has one of the formulas:

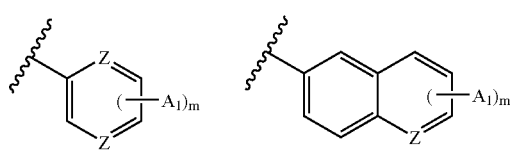

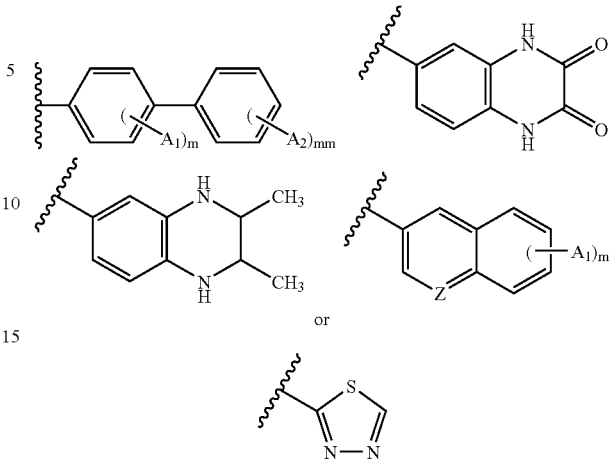

wherein each Z is, independently, CH or N; each $A_1$ and $A_2$ is, independently, halogen, hydroxyl, amino, $C_1$-$C_6$ alkyl, $C_2$-$C_6$ alkenyl, $C_2$-$C_6$ alkynyl or alkoxy; n is from 1 to about 6; m is 0, 1, 2, 3 or 4; and mm is 0, 1, 2, 3, 4 or 5.

Preferably, $J_4$ has one of the formulas:

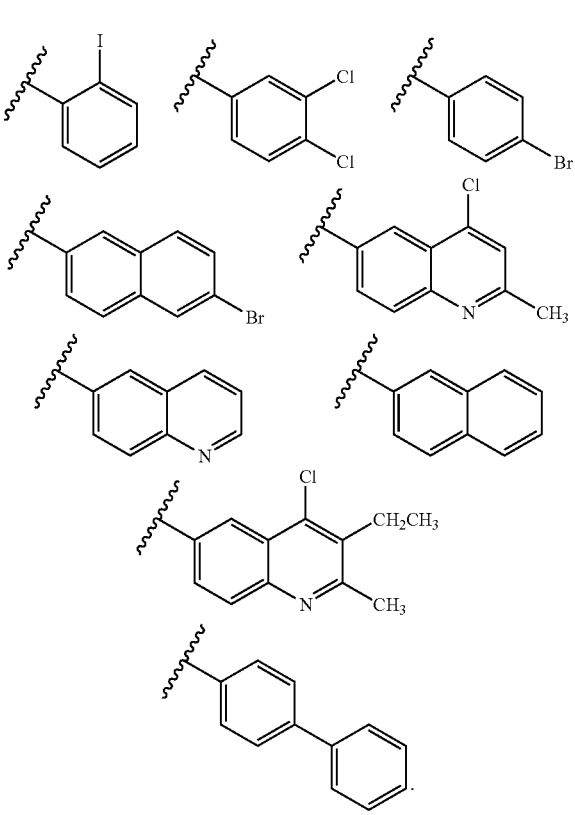

In some preferred embodiments where $J_4$ is one of these formulas, $L_1$ is C(=O). In other embodiments, $L_1$ is C(=O) and $J_2$ is -p-$C_6H_4$—O—$(CH_2)_n$—$NR_3R_4$. In yet another embodiment, $L_1$ is C(=O), $J_2$ is -p-$C_6H_4$—O—$(CH_2)_n$—$NR_3R_4$, and $R_3$ and $R_4$ are each $CH_3$.

In certain preferred embodiments, compounds of the invention have the formula:

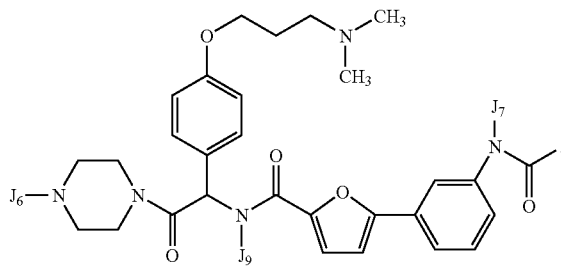

wherein $J_6$ is or H or $C_1$-$C_8$ alkyl;

$J_8$ has one of the formulas:

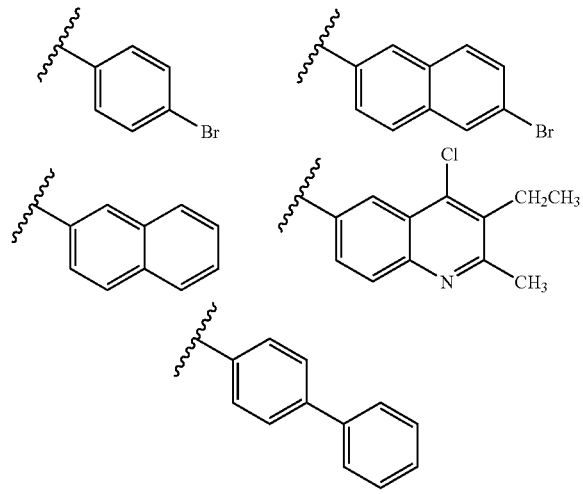

each $J_7$ and $J_9$ is, independently, H or $C_1$-$C_6$ alkyl

Other embodiments of invention are methods of treating bacterial infection in a mammal by administering to the mammal an effective amount of a compound described herein.

In a preferred embodiment the mammal to be treated is a human.

In some embodiments, the bacteria behind the bacterial infection is at least one of *Streptococcus pyogenes, Enterococcus faecalis, Escherichia coli, Klebsiella pneumoniae* or *Staphylococcus aureus*.

In another aspect of the invention there is provided a method of treating bacterial infection in a mammal comprising administering to said mammal an effective amount of a biaryl compound of the invention.

"Hydrocarbyl" groups are aliphatic or carbocyclic groups. Aliphatic hydrocarbyl groups according to the invention include saturated (i.e., alkyl) and unsaturated (i.e., alkenyl and alkynyl) which are straight or branched chains having from 1 to about 12 carbon atoms in length, and preferably 1-6 carbons and most preferably 1-4 carbons, e.g., methyl, ethyl, propyl, i-propyl, butyl, i-butyl, s-butyl and t-butyl. "Carbocyclic" hydrocarbyl groups include 3 to about 16 membered, mono-, bi- or tricyclic carbon ring systems which are saturated or unsaturated. Preferred carbocyclic groups include cycloalkyl (e.g. cyclopropyl, cyclobutyl, cyclopentyl and cyclohexyl) and aryl (e.g., phenyl, naphthyl, anthracenyl and phenanthrenyl).

"Heterocyclic ring system," "heterocyclic ring," and "heterocycle" as used herein are meant to include a mono or poly cyclic compound having at least one ring that has at least one N, O or S atom imbedded therein. The individual cyclic rings that comprise each heterocyclic ring system of the present invention can be saturated, partially or unsaturated thereby including heteroaryl ring systems. A heteroaryl compound is a heterocycle containing at least one hetero atom such as N, O, or S and is not fully saturated e.g. is in a state of partial or complete saturation. Heteroaryl is also meant to include fused systems including systems where one or more of the fused rings contain no heteroatoms. Heterocyclic ring systems include single or multiply fused ring systems that are optionally mono or poly substituted with other functional groups. Heterocyclic ring systems amenable to the present invention include but are not limited to epoxide, oxetane, tetrahydrofuran, tetrahydropyran, dihydropyran, dioxane, trioxane, ethylenesulfide, thietane, tetrahydrothiophene, tetrahydrothiopyran, dithiane, trithiane, aziridine, azetidine, pyrrolidine, piperidine, homopiperidine, piperazine, homopiperazine, triazine, quinuclidine, decahydroquinoline, oxazole, morpholine, thiazolidine, thiomorpholine, gamma-butyrolactone, delta-valerolactone and thiolactone. Preferred ring systems include from about 5 to 16 membered, mono-, bi-, or tricyclic ring systems. Some representative preferred heterocyclic ring systems amenable to the present invention include, but are not limited to, imidazole, pyrrole, pyrazole, indole, 1H-indazole, α-carboline, carbazole, phenothiazine, phenoxazine, tetrazole, triazole, pyrrolidine, piperidine, piperazine and morpholine groups. A more preferred group of nitrogen heterocycles includes imidazole, pyrrole, and carbazole groups. The heterocycle is attached via a covalent bond to either a heteroatom or a carbon atom of the ring system. It will be appreciated by the skilled artisan that attachment depends on the particular heterocycle and group from which it depends.

It will be appreciated that compounds of the invention may incorporate chiral centers and therefore exist as geometric and stereoisomers. All such isomers are contemplated and are within the scope of the invention whether in pure isomeric form or in mixtures of such isomers as well as racemates.

Compounds of the invention may be prepared according to established organic synthetic techniques from starting materials and reagents that are commercially available. In a particular embodiment, biaryl compounds of the invention are prepared by coupling the two aryl moieties, an A ring and a B ring.

Coupling may be achieved by a Suzuki reaction wherein an iodo or bromo derivatized A or B ring is reacted with the other of the A or B ring which is derivatized with a boronic acid substituent. The reaction occurs in the presence of a typical Suzuki reaction catalyst such as tetrakis-triphenylphosphine palladium (Pd(PPh$_3$)$_4$) and in a polar solvent such as ethyleneglycol dimethyl ether (DME) at elevated temperature (about 70° C.) over several hours, wherein the boronic acid ring intermediate is provided in molar excess (about 7 equivalents) relative to the iodo ring intermediate.

The coupling of the A and B ring will yield the desired final biaryl compound. It will be appreciated by those skilled in the art of organic chemistry that, depending on the structure of the various substituents, protection and deprotection steps may be necessary to achieve the desired compound of the invention. Suitable protecting groups and their preparation are described in detail in Greene and Wuts (Protective Groups in Organic Chemistry, 2d edition, John Wiley and Sons, 1991)* herein incorporated by reference. For example, suitable amine protecting groups include t-butyloxycarbonyl (Boc), fluorenyl-methyloxycarbonyl (Fmoc), 2-trimethylsilyl-ethyoxycarbonyl (Teoc), 1-methyl-1-(4-biphenylyl)ethoxycarbonyl (Bpoc), allyloxycarbonyl (Alloc), and benzyloxycarbonyl (Cbz). Suitable carboxyl protecting groups include alkyl esters such as acetyl (Ac), methoxymethyl (MOM), methylthiomethyl (MTM), terahydropyranyl (TMP), methoxyethoxymethyl (MEM) and benzyloxymethyl (BOM).

Compounds of the invention may also be prepared by first coupling the A and B rings as previously described and subsequently appending the desired substituents. For example, a carboxyl substituted A ring may be coupled to an amino substituted B ring.

One of the carboxyl or amino groups on the A and B rings is preferably protected prior to the Suzuki coupling of the rings. Following coupling, the free amine or carboxyl group may then be acylated.

Alternatively, compounds of the invention may be prepared using solid phase techniques wherein a substituent group of the compound is bound to a solid support (resin) and reacted with appropriate reagents to arrive at the final compound. For example, a carboxyl substituted A ring may be bound to an amine-derivatized support by formation of an amide bond. The A ring could then be subjected to Suzuki coupling reaction with a B ring.

The bound intermediate compound is cleaved from the solid support with a suitable reagent such as TFA resulting in a free amide group which then may be derivatized to achieve compounds of the invention. Alternatively, the B ring may be bound to a carboxyl derivatized support and subsequently coupled to the A ring.

Cleavage from the support by a suitable cleaving reagent such as TEA yields an intermediate with a free amine which may then be acylated to yield the desired compound of the invention. It will be appreciated that compounds of the invention may be prepared by solid phase techniques wherein any of the substituent groups may be bound to the solid support.

In a particularly preferred embodiment, compounds of the invention are prepared by solid phase chemical techniques employing the IRORI MicroKan™ solid phase approach as described by Xiao et al (Biotechnol. Bioeng., 2000, 71(1): 44). MicroKan™ microreactors are rigid containers containing a solid phase resin with mesh side walls in which a single compound is synthesized. Synthesis takes place by allowing reagents to flow through the outer mesh walls of the microreactor using normal laboratory glassware, heating apparatus, cooling apparatus and mixers. Each container further incorporates a miniature radiofrequency (Rf) label for sorting and tracking the particular compound during the synthetic process.

According to an aspect of the invention, there is provided a method of treating bacterial infection in a mammal comprising administering to said mammal, for example a human, an effective amount of a compound of the invention. By "effective amount" is meant an amount of compound which upon administration is capable of reducing or preventing proliferation of the bacteria or reducing or preventing symptoms associated with the bacterial infection. Particular bacteria treatable upon administration of compounds of the invention include *K. pneumoniae, E. coli, S. aureus, E. faecalis* and *M. tuberculosis*. The actual amount of compound administered and the route of administration will depend upon the particular disease or bacteria as well as other factors such as the size, age, sex and ethnic origin of the individual being treated and is determined by routine analysis. In methods of the invention, the compound may be administered orally (including buccal, sublingual, inhalation), nasally, rectally, vaginally, intravenously, intradermally, subcutaneously and topically. Compounds will be formulated into compositions suitable for administration for example with suitable carriers, diluents, thickeners, adjuvants etc as are routine in the formulation art. Compositions of the invention may also include additional active ingredients. Dosage forms include solutions, powders, tablets, capsules, gel capsules, suppositories, topical ointments and creams and aerosols for inhalation.

Formulations for non-parenteral administration may include sterile aqueous solutions which may also contain buffers, diluents and other suitable additives. Pharmaceutically acceptable organic or inorganic carrier substances suitable for non-parenteral administration which do not deleteriously react with compounds of the invention can be used. Suitable pharmaceutically acceptable carriers include, but are not limited to, water, salt solutions, alcohol, polyethylene glycols, gelatin, lactose, amylose, magnesium stearate, talc, silicic acid, viscous paraffin, hydroxymethylcellulose, polyvinylpyrrolidone and the like. The formulations can be sterilized and, if desired, mixed with auxiliary agents, e.g., lubricants, preservatives, stabilizers, wetting agents, emulsifiers, salts for influencing osmotic pressure, buffers, colorings, flavorings and/or aromatic substances and the like which do not deleteriously react with compounds of the invention. Aqueous suspensions may contain substances which increase the viscosity of the suspension including, for example, sodium carboxymethylcellulose, sorbitol and/or dextran. Optionally, the suspension may also contain stabilizers.

In a preferred embodiment, compounds of the invention are administered via oral delivery. Compositions for oral administration include powders or granules, suspensions or solutions in water or non-aqueous media, capsules, sachets, troches, tablets or SECs (soft elastic capsules or caplets). Thickeners, flavoring agents, diluents, emulsifiers, dispersing aids, carrier substances or binders may be desirably added to such formulations. The use of such formulations has the effect of delivering the nucleic acid to the alimentary canal for exposure to the mucosa thereof. Accordingly, the formulation can consist of material effective in protecting the compound from pH extremes of the stomach, or in releasing the compound over time, to optimize the delivery thereof to a particular mucosal site. Enteric coatings for acid-resistant tablets, capsules and caplets are known in the art and typically include acetate phthalate, propylene glycol and sorbitan monoleate.

Various methods for producing formulations for alimentary delivery are well known in the art. See, generally, Naim, Chapter 83; Block, Chapter 87; Rudnic et al., Chapter 89; Porter, Chapter 90; and Longer et al., Chapter 91 In: *Remington=s Pharmaceutical Sciences,* 18th Ed., Gennaro, ed., Mack Publishing Co., Easton, Pa., 1990. The formulations of the invention can be converted in a known manner into the customary formulations, such as tablets, coated tablets, pills, granules, aerosols, syrups, emulsions, suspensions and solutions, using inert, non-toxic, pharmaceutically suitable excipients or solvents. The therapeutically active compound should in each case be present in a concentration of about 0.5% to about 95% by weight of the total mixture, i.e., in amounts which are sufficient to achieve the desired dosage range. The formulations are prepared, for example, by extending the active compounds with solvents and/or excipients, if appropriate using emulsifying agents and/or dispersing agents, and, for example, in the case where water is used as the diluent, organic solvents can be used as auxiliary solvents if appropriate.

Compositions may be formulated in a conventional manner using additional pharmaceutically acceptable carriers or excipients as appropriate. Thus, the composition may be prepared by conventional means with additional carriers or excipients such as binding agents (e.g., pregelatinised maize starch, polyvinylpyrrolidone or hydroxypropyl methylcellulose); fillers (e.g., lactose, microcrystalline cellulose or calcium hydrogen phosphate); lubricants (e.g., magnesium stearate, talc or silica); disintegrates (e.g., starch or sodium starch glycolate); or wetting agents (e.g., sodium lauryl sulfate). Tablets may be coated by methods well known in the art. The preparations may also contain flavoring, coloring and/or sweetening agents as appropriate.

The pharmaceutical formulations, which may conveniently be presented in unit dosage form, may be prepared according to conventional techniques well known in the pharmaceutical industry. Such techniques include the step of bringing into association the active ingredients with the pharmaceutical carrier(s) or excipient(s). In general the formulations are prepared by uniformly and intimately bringing into association the active ingredients with liquid carriers or finely divided solid carriers or both, and then, if necessary, shaping the product.

Formulations of the present invention suitable for oral administration may be presented as discrete units such as capsules, cachets or tablets each containing predetermined amounts of the active ingredients; as powders or granules; as solutions or suspensions in an aqueous liquid or a non-aqueous liquid; or as oil-in-water emulsions or water-in-oil liquid emulsions. A tablet may be made by compression or molding, optionally with one or more accessory ingredients. Compressed tablets may be prepared by compressing in a suitable machine, the active ingredients in a free-flowing form such as a powder or granules, optionally mixed with a binder, lubricant, inert diluent, preservative, surface active or dispersing agent. Molded tablets may be made by molding in a suitable machine a mixture of the powdered compound moistened with an inert liquid diluent. The tablets may optionally be coated or scored and may be formulated so as to provide slow or controlled release of the active ingredients therein.

Furthermore, compounds of the invention may be used as sterilizing agents, for example as an additive or component in scrub solutions for surfaces (i.e., glassware) or in laundering compositions.

EXAMPLE 1

General Procedure for Preparing Biaryl Compounds and Similar Analogs

Compounds having the general formula I:

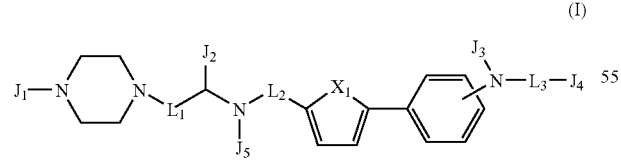

(I)

wherein $X_1$ is $CH_2$, O, S or NH;

each $L_1$, $L_2$ and $L_3$ is, independently, $CR_1R_2$, C=O or S(=O)(=O);

each $R_1$ and $R_2$ is, independently, H or $C_1$-$C_6$ alkyl;

$J_1$ is or H, $C_1$-$C_8$ alkyl; C(=O)O-alkyl or S(=O)(=O)-alkyl;

$J_2$ is —$(CH_2)_n$—$NR_3R_4$ or -p-$C_6H_4$—O—$(CH_2)_n$—$NR_3R_4$;

each $R_3$ and $R_4$ is, independently, H or $C_1$-$C_6$ alkyl;

each $J_3$ and $J_5$ is, independently, H or $C_1$-$C_6$ alkyl;

$J_4$ is a single or multiple ring system comprising one or more substituted or unsubstituted aromatic and/or heterocyclic rings that can be present alone, fused or linked together to form a variety of different ring configurations. The heterocyclic rings can be unsaturated, saturated or at some state between e.g. partially saturated. Substituent groups can be present at any available site in each of the rings present. Preferred substituent groups include hydroxyl, amino, alkoxy, carboxy, benzyl, phenyl, nitro, thiol, thioalkoxy, halogen, alkyl, aryl, alkenyl and alkynyl. Some preferred ring systems which are meant to be representative and not limiting are listed below:

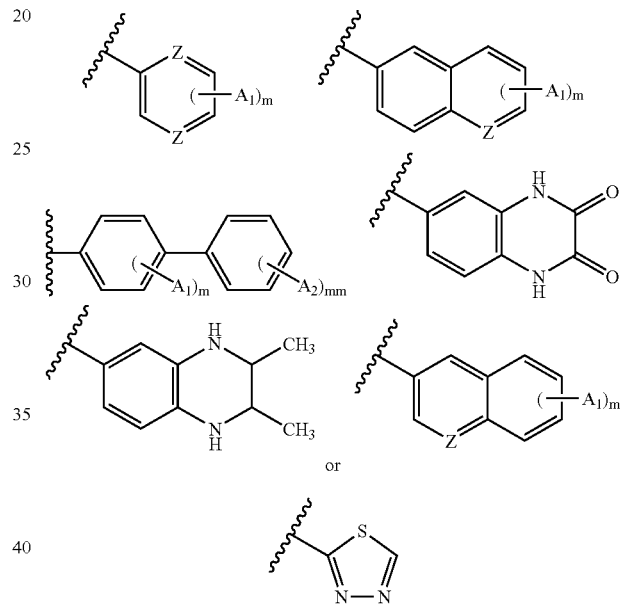

wherein:

each Z is, independently, CH or N;

each $A_1$ and $A_2$ is, independently, a substituent group selected from hydroxyl, amino, alkoxy, carboxy, benzyl, phenyl, nitro, thiol, thioalkoxy, halogen, alkyl, aryl, alkenyl and alkynyl;

n is from 1 to about 6;

m is 0, 1, 2, 3 or 4; and mm is 0, 1, 2, 3, 4 or 5;

are prepared following the solid phase route outlined in Scheme 1. In the synthesis, an Fmoc-protected amino acid is coupled to piperazine-derivatized ArgoGel™ Wang resin, deprotected, and then allowed to react with 5-bromofuroic acid. A key Suzuki cross coupling reaction with 3-nitrophenylboronic acid provides the biaryl core. After aryl nitro group reduction, the amine is reacted with either a carboxylic acid or a sulfonyl chloride. All compounds were cleaved from the resin in >80% purity and purified by reversed-phase HPLC to >95% homogeneity (isolated as AcOH salts in most cases). Spectral data was obtained for all compounds (LC-MS and $^1$H NMR) and was consistent with the proposed structures.

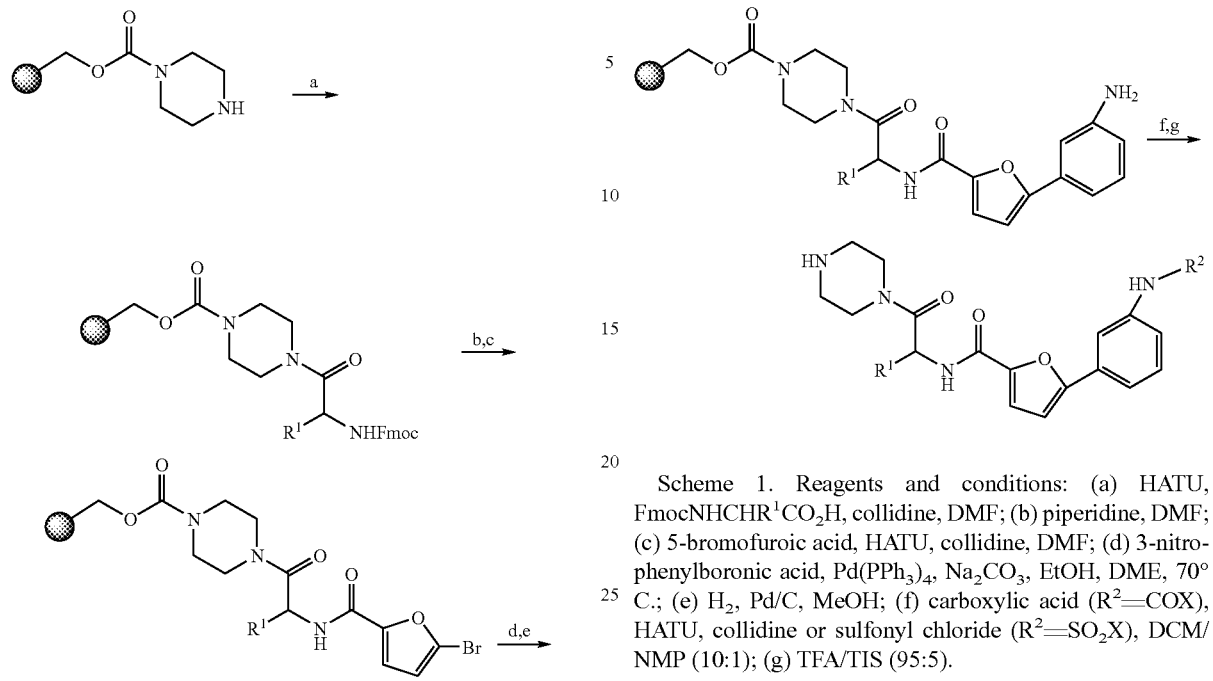

Scheme 1. Reagents and conditions: (a) HATU, FmocNHCHR¹CO₂H, collidine, DMF; (b) piperidine, DMF; (c) 5-bromofuroic acid, HATU, collidine, DMF; (d) 3-nitrophenylboronic acid, Pd(PPh$_3$)$_4$, Na$_2$CO$_3$, EtOH, DME, 70° C.; (e) H$_2$, Pd/C, MeOH; (f) carboxylic acid (R$^2$=COX), HATU, collidine or sulfonyl chloride (R$^2$=SO$_2$X), DCM/NMP (10:1); (g) TFA/TIS (95:5).

EXAMPLE 2

TABLE 1

Protein synthesis inhibitory activity of biaryls against *E. coli*.

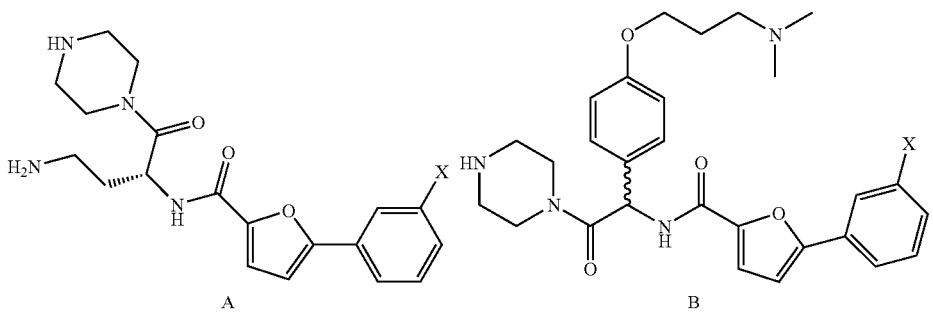

| Comp | X | Struct | IC$_{50}$: M[a,b] | Comp | Struct | IC$_{50}$: M[a,b] |
|---|---|---|---|---|---|---|
| 3[c] | ![](methylcarbamoyl-quinoxalinedione) | A | 14 | 12 | B | 3 |
| 4 | —NH₂ (methylamine) | A | >100 | 13 | B | >100 |
| 5 | ![](methylsulfamoyl-quinoxalinedione) | A | >100 | 14 | B | 33 |

TABLE 1-continued

Protein synthesis inhibitory activity of biaryls against *E. coli*.

| Comp | X | Struct | IC$_{50}$, :M$^{a,b}$ | Comp | Struct | IC$_{50}$: M$^{a,b}$ |
|---|---|---|---|---|---|---|
| 6 | *N-methylcarboxamide-2,3-dichloroquinoxaline* | A | 15 | 15 | B | 1 |
| 7 | *N-methylquinoline-3-carboxamide* | A | 46 | 16 | B | 5 |
| 8 | *N-methylpyridine-2-carboxamide* | A | >100 | 17 | B | 20 |
| 9 | *N-methylpyrazine-2-carboxamide* | A | >100 | 18 | B | 15 |
| 10 | *N-methyl-1,3,4-thiadiazole-2-carboxamide* | A | >100 | 19 | B | 13 |

TABLE 1-continued

Protein synthesis inhibitory activity of biaryls against *E. coli*.

| Comp | X | Struct | IC$_{50}$, :M$^{a,b}$ | Comp | Struct | IC$_{50}$,: M$^{a,b}$ |
|---|---|---|---|---|---|---|
| 11 | (see structure) | A | >100 | 20 | B | >100 |

[a] In vitro bacterial protein synthesis inhibition (*E. coli* extract).
[b] Compounds did not display MIC activity at 100 :M (<75% inhibition) against *E. coli*. and *S. aureus* bacterial strains.
[c] IC$_{50}$ = 14 :M for enantiomer.

Since in vitro MIC activity was not obtainable by replacing the quinoxalinedione functionality with a series of less hydrophilic substituents, another portion of biaryl 3 was modified. By employing SAR by MS strategy it was found that analogues of the binding motif,

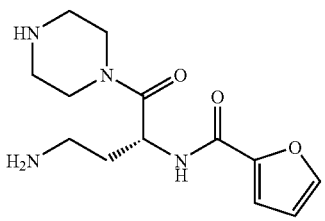

($K_d$=50 μM), lacking cationic side chains bound poorly to the A1061 23S rRNA MS screening construct. Presumably, without being bound by this theory, the cationic aminoethyl side chain interacts with a negatively charged phosphate of the RNA MS target. From other RNA-targeted drug discovery programs, the dimethylaminoalkoxy was identified as an interesting RNA-recognition motif. See Maier, M. A.; Leeds, J. M.; Balow, G.; Springer, R. H.; Bharadwaj, R.; Manoharan, M. *Biochemistry* 2002, 41, 1323-1327; and Wyatt, P. G.; Bethell, R. C.; Cammack, N.; Charon, D.; Dodic, N.; Dumaitre, B.; Evans, D. N.; Green, D. V. S.; Hopewell, P. L.; et al. *Journal of Medicinal Chemistry* 1995, 38, 1657-1665. The aminoethyl side-chain of 3 was substituted with a modification based on this motif. Since both enantiomers of biaryl 3 gave identical IC$_{50}$ values in the bacterial protein synthesis assay, a cationic tyrosine-type moiety was incorporated into the SAR plan via the commercially available racemic building block (Scheme 5) (PharmaCore, Inc., High Point, N.C.).

One of the closest analogues of biaryl 3 with the dimethylaminopropoxyphenyl modification was found to be ~5-fold more potent (Table 1, compound 12, IC$_{50}$=3:M). However, the compound still lacked MIC activity in initial antibacterial screens at 100:M. Incorporating the new side-chain into the SAR study, the end-group modifications made to parent lead structure 3 were reexplored. As with biaryl 4, removing the quinoxalinedione group abolished the antibacterial activity for biaryl 13. However biaryl 14, with the sulfonylamide link is >3-fold more potent than analogue 5 and dimethylquinoxaline-substituted biaryl 15 is ~15-fold more potent than analogue 6. Furthermore, the activity of the quinoline-substituted biaryl 16 was improved ~10-fold relative to biaryl 7. With the dimethylaminopropoxyphenyl side-chain modification, the monocyclic end-group analogues are tolerated (biaryls 17-19). Some fragmented structures (21, 22) were also explored to assess the importance of the piperazine and the biaryl pharmacophores. Biaryl 21, lacking the piperazine functionality, is ~3-fold less potent than 12 while compound 22, lacking the biaryl core, is inactive at 200:M. Like the aminoethyl series, the cationic end-group of 20 was not tolerated. Compounds 13-22 were not active in our initial MIC assays at 100 :M presumably still suffering from poor cell permeability and/or intracellular efflux.

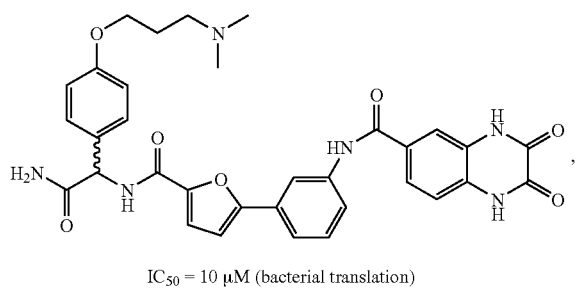

21

IC$_{50}$ = 10 μM (bacterial translation)

22

IC$_{50}$ > 200 μM

Since a wider variety of end-groups were tolerated for the new biaryl series in the protein synthesis assay, additional substitutions, including more hydrophobic substitutions (Table 2) were explored. The acetamide and cyclohexane end-group substitutions (compounds 23 and 24) abolished the in vitro antibacterial activity. The quinoline substituted analogues (25 versus 16) gave similar inhibitory activities. The phenyl substituted biaryl gave similar inhibitory activity as the 2-iodophenyl analogue (26 versus 27). The dichlorophenyl substituted analog was ~10-fold superior with an IC$_{50}$ of 4:M. The more lipophilic quinoline end-group gave a 3-fold improvement in antibacterial activity compared to quinoline-substituted biaryl 25. None of the compounds in Table 2 displayed MIC activity in our primary antibacterial screens at 100:M.

TABLE 2

Protein synthesis inhibitory activity of biaryls against *E. coli*.

| Compd | X | IC$_{50}$, :M$^{a,b}$ |
|---|---|---|
| 23 | (N-methylacetamide) | >100 |
| 24 | (N-methylcyclohexanecarboxamide) | >100 |
| 25 | (N-methylquinoline-6-carboxamide) | 6 |
| 26 | (N-methylbenzamide) | 40 |
| 27 | (N-methyl-2-methylbenzamide) | 38 |
| 28 | (N-methyl-3,4-dichlorobenzamide) | 4 |
| 29 | (N-methyl-4-chloro-2-methylquinoline-6-carboxamide) | 2 |

$^{a}$In vitro bacterial translation inhibition (*E. coli* extract).
$^{b}$Compounds did not display MIC activity at 100: M (<75% inhibition) against *E. coli*. and *S. aureus* bacterial strains.

Additional end-group modifications, including some biaryls were discovered to display MIC activity in primary screens (Table 3). The bromophenyl-substituted analogue displayed similar low :M inhibitory activity as its dichorophenyl analogue (30 versus 28). However, unlike biaryl 28, biaryl 30 gave good MIC activity against *E. coli* and *S. aureus* pathogens. The naphthalene substitution gave a 4-fold better IC$_{50}$ than its phenyl analogue in the cell-free assay (31 versus 26) as well as displaying some weak MIC activity. The aryl-bromo substitution also improves antibacterial activity (32 versus 31 and 30 versus 26) and the incorporation of ethyl to the end-group of 29 led to MIC-active analogue 33.

The biphenyl substitution improves in vitro antibacterial inactivity 4-fold compared to the phenyl substitution (34 versus 26). Unlike 26, 34 shows good MIC activity in initial screens (MIC=3-6:M versus *S. aureus* and 6-13:M versus *E. coli*). Biaryl 34 was selected to be evaluated against some additional bacterial strains. The analogue shows MIC activity against Gram-positive *Enterococcus faecalis* and *Streptococcus pyogenes* (3-6:M) and Gram-negative *Klebsiella pneumoniae* (13-25:M) and *Proteus vulgaris* (50-100:M). (Bacterial strains: *S. pyogenes* ATCC 49399, *E. faecalis* ATCC 29212, *K pneumoniae* ATCC 13383, *P. vulgaris* ATCC 8427 and methicillin resistant *S. aureus* ATCC43300.) Furthermore, biaryl 34 was found to be active against a methicillin-resistant *S. aureus* strain at 13-25:M. This is an especially important finding as multi-drug resistant *S. aureus* is a serious clinical problem. Finally, we confirmed that biaryl 34 is selective for bacterial protein synthesis inhibition as it was found not to inhibit eukaryotic protein synthesis at 200:M in a cell-free assay. See Kung, P.-P.; Casper, M. D.; Cook, K. L.; Wilson-Lingardo, L.; Risen, L. M.; Vickers, T. A.; Ranken, R.; Blyn, L. B.; Wyatt, J. R.; Cook, P. D.; Ecker, D. J. *J. Med. Chem.* 1999, 42, 4705-4713.

TABLE 3

Protein synthesis inhibitory activity for *E. coli* protein synthesis and MIC activity.

| Compd | X | IC$_{50}$, :M[a] | MIC (:M) *E. coli*[b] | MIC (:M) *S. aureus*[b] |
|---|---|---|---|---|
| 30 | 4-bromo-N-methylbenzamide | 5 | 6-13 | 13-25 |
| 31 | N-methyl-2-naphthamide | 10 | 25-50 | 50-100 |
| 32 | 6-bromo-N-methyl-2-naphthamide | 5 | 6-13 | 13-25 |
| 33 | 4-chloro-3-ethyl-2-methyl-N-methylquinoline-6-carboxamide | 0.78 | 13-25 | >100 |
| 34 | N-methyl-4-phenylbenzamide (biphenyl) | 9 | 6-13 | 3-6 |

[a] In vitro bacterial translation inhibition (*E. coli* extract).
[b] Bacterial strains: *E. coli* ATCC 25922, *S. aureus* ATCC 13709.

EXAMPLE 3

Derivatives of biaryl 34, were synthesized and assessed according to the procedures discussed above. Several derivatives having a substitution on the second, B-ring, of the biphenyl were made

TABLE 4

Protein synthesis inhibitory activity and MIC activity of derivatives of compound 34

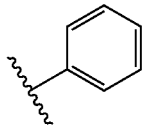

| Comp | R | translation IC$_{50}$ (mM) | MIC, mM (E. coli) | MIC, mM (S. aureus) |
|---|---|---|---|---|
| 34 | 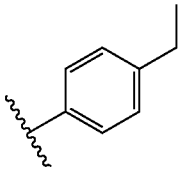 | 9 | 6-13 | 6-13 |
| | Biphenyl B-Ring Alkyl substitutions | | | |
| 35 | 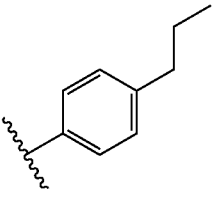 | 13 | 50-100 | 6-13 |
| 36 | 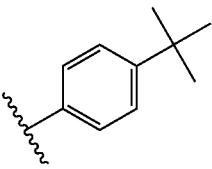 | >200 | >100 | 13-25 |
| 37 | 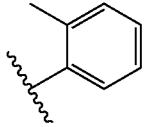 | >200 | >100 | >100 |
| 38 | 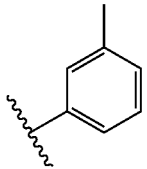 | 4 | 3-6 | 3-6 |
| 39 | 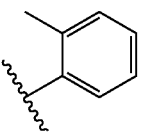 | 6 | 13-25 | 13-25 |// 
| 40 | 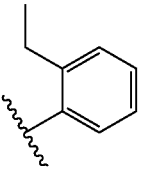 | 4 | 3-6 | 3-6 |
| 41 | 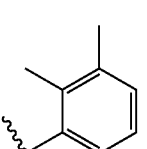 | 9 | 13-25 | 3-6 |
| 42 | 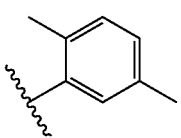 | >200 | 13-25 | 3-6 |
| 43 | 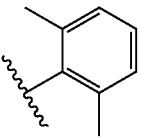 | 50 | 25-50 | 13-25 |
| 44 | 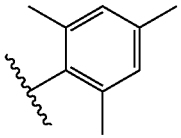 | 50 | 25-50 | 13-25 |
| 45 | 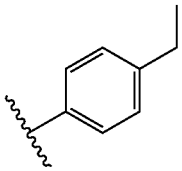 | >200 | 50-100 | 13-25 |
| 46 |  | 22 | NA | NA |

TABLE 4-continued
Protein synthesis inhibitory activity and MIC activity of derivatives of compound 34
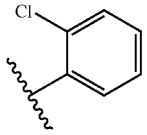
| Comp | R | translation IC$_{50}$ (mM) | MIC, mM (E. coli) | MIC, mM (S. aureus) |
|---|---|---|---|---|
| *B-Ring Cl Substitutions* | | | | |
| 47 | 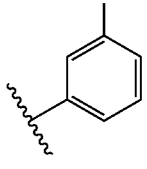 | >200 | 6-13 | 25-50 |
| 48 | 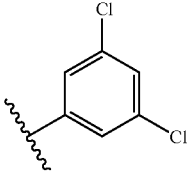 | 1.4 | 13-25 | 13-25 |
| 49 | 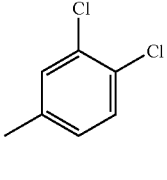 | >200 | >100 | >100 |
| 50 | 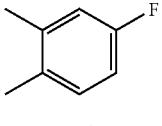 | >200 | >100 | >100 |
| *B-Ring F Substitutions* | | | | |
| 51 | 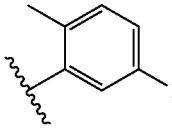 | 96 | 625-50 | 6-13 |
| 52 | 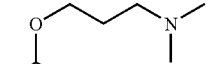 | 110 | 13-25 | 6-13 |
| 53 | 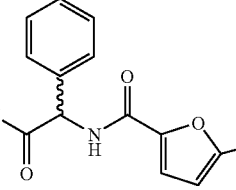 | 3 | 13-25 | 6-13 |
| 54 | 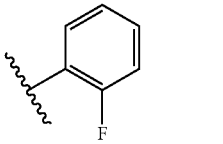 | 38 | 3-6 | 13-25 |
| 55 | 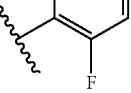 | 12 | 25-50 | 6-13 |
| 56 | 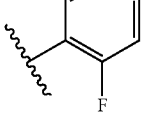 | 12 | N/A | N/A |
| 57 | 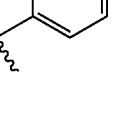 | 9 | N/A | N/A |
| 58 | 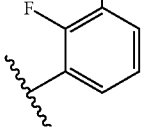 | 4 | N/A | N/A |

EXAMPLE 4

Other derivatives were made with substitution to the first, A-ring of the biphenyl group of biaryl 34.

TABLE 5

Protein synthesis inhibitory activity and MIC activity of derivative of compound 34

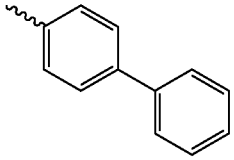

| Comp. | R | translation IC$_{50}$ (mM) | MIC, mM (E. coli) | MIC, mM (S. aureus) |
|---|---|---|---|---|
| 34 | (4-biphenyl) | 9 | 6-13 | 3-6 |
| 59 | (3-F-4-biphenyl) | 15 | 3-6 | 6-13 |
| 60 | (3-Cl-4-biphenyl) | 45 | 6-13 | 25-50 |
| 61 | (3-Me-4-biphenyl) | 15 | N/A | N/A |
| 62 | (2-Me-4-biphenyl) | 41 | 3-6 | 12-25 |
| 63 | (2,3,5,6-tetraF-4-biphenyl) | 13 | N/A | N/A |

EXAMPLE 5

Given the success of the biphenyl substitution, other derivatives were made, maintaining the biphenyl group with various other modifications, including amid bond modifications, dimehtylamino side chain modifications, thiophene derivatives, and piperizine derivatives.

TABLE 6
Protein synthesis inhibitory activity and MIC activity of derivatives of
compound 34 maintaining the biphenyl group with amide bond modifications.
Amide Bond Modifications
| Compound | | translation IC50 (mM) | MIC, mM (*E. coli*) | MIC, mM (*S. aureus*) |
|---|---|---|---|---|
| 34 | 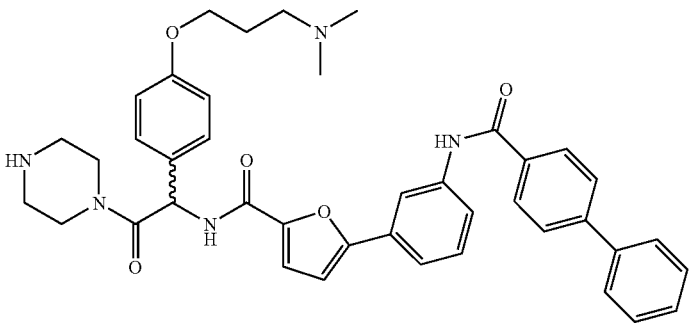 | 9 | 6-13 | 3-6 |
| 64 | 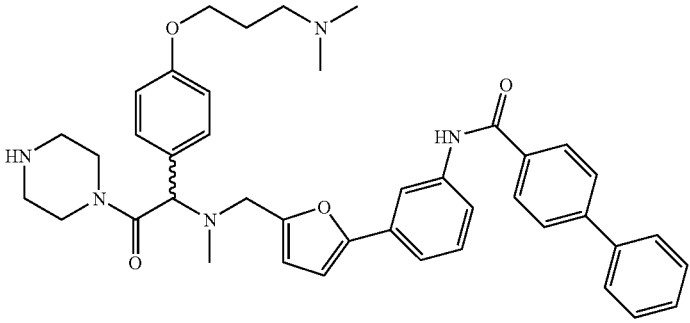 | 92 | 6-13 | 3-6 |
| 65 | 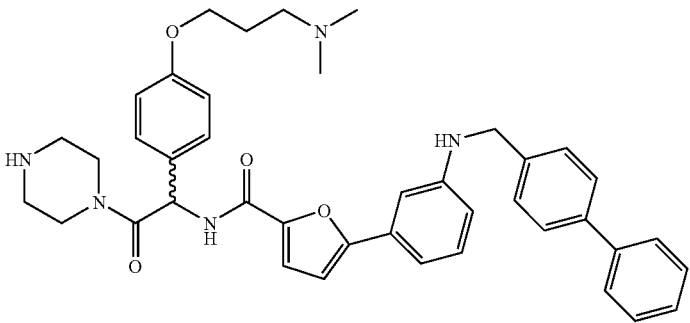 | >200 | 13-25 | 3-6 |

TABLE 6-continued

Protein synthesis inhibitory activity and MIC activity of derivatives of
compound 34 maintaining the biphenyl group with amide bond modifications.
Amide Bond Modifications

| Compound | translation IC50 (mM) | MIC, mM (E. coli) | MIC, mM (S. aureus) |
|---|---|---|---|
| 66 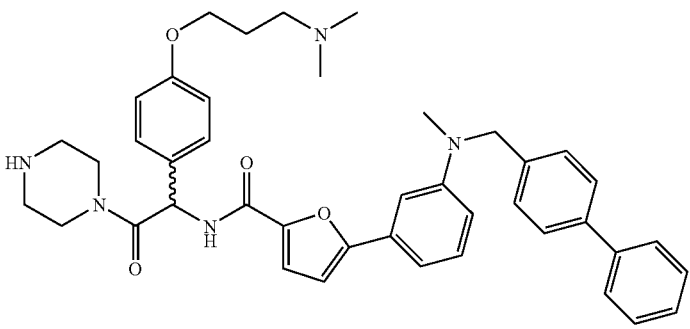 | 95 | 13-25 | 3-6 |
| 67 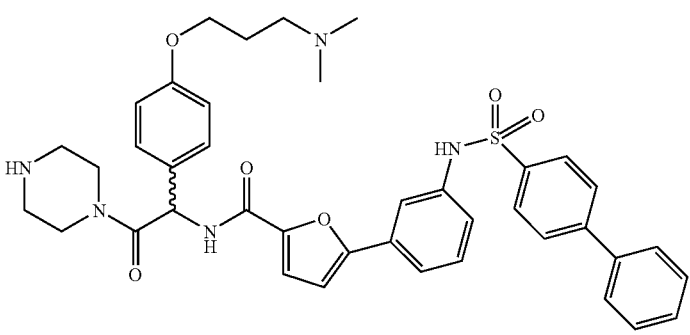 | >200 | 50-100 | 25-50 |

TABLE 7

Protein synthesis inhibitory activity and MIC activity of derivatives of
compound 34 maintaining the biphenyl group with Dimethylamino side chain modifications.
Dimethylamino side chain modification

| Compound | translation IC50 (mM) | MIC, mM (E. coli) | MIC, mM (S. aureus) |
|---|---|---|---|
| 34 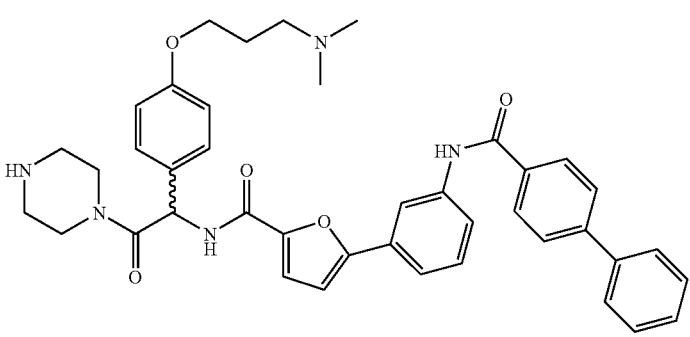 | 9 | 6-13 | 3-6 |

| | | | | |
|---|---|---|---|---|
| 68 | 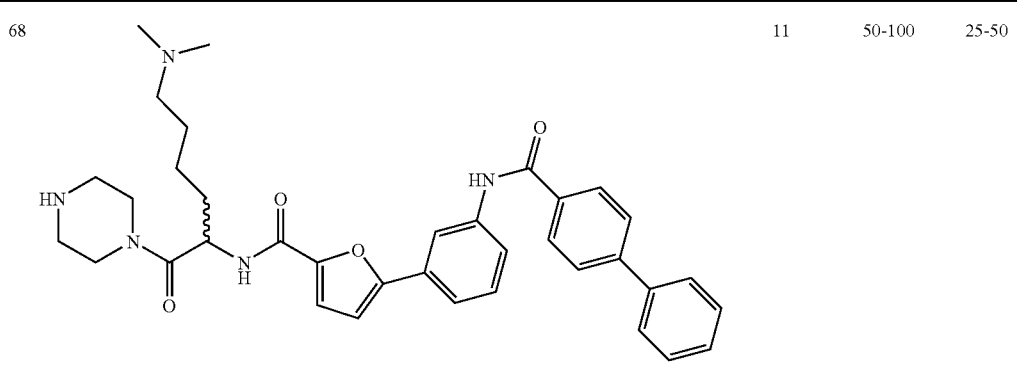 | 11 | 50-100 | 25-50 |
Protein synthesis inhibitory activity and MIC activity of derivatives of
compound 34 maintaining the biphenyl group, where X is S rather than O.
Thiophene vs. furan
| | | translation IC50 (mM) | MIC, mM (*E. coli*) | MIC, mM (*S. aureus*) |
|---|---|---|---|---|
| 34 | 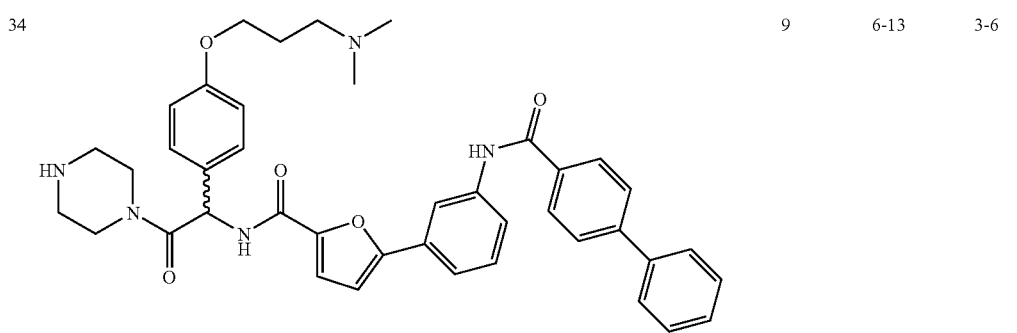 | 9 | 6-13 | 3-6 |
| 69 | 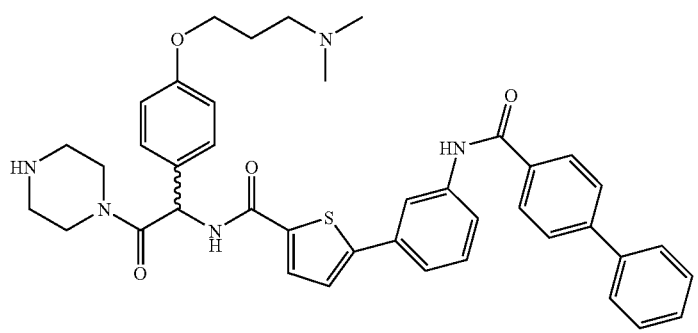 | 40 | 25-50 | 25-50 |

TABLE 8

Protein synthesis inhibitory activity and MIC activity of derivatives of compound 34 maintaining the biphenyl group with a piperazine modification.

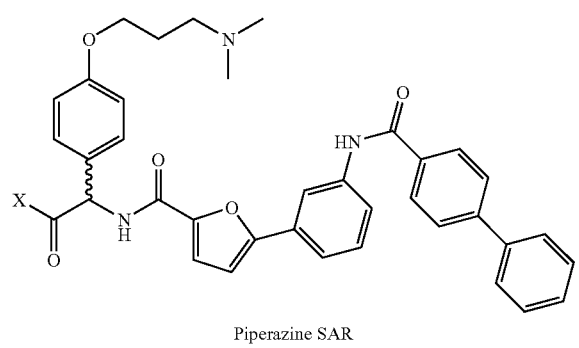

Piperazine SAR

| | X | translation IC50 (mM) | MIC, mM (E. coli) | MIC, mM (S. aureus) |
|---|---|---|---|---|
| 34 | (piperazine, HN) | 9 | 6-13 | 3-6 |
| 70 | (N-methylpiperazine) | 40 | 25-50 | 25-50 |
| 71 | (methylsulfonylpiperazine) | >100 | >100 | >100 |

TABLE 8-continued

Protein synthesis inhibitory activity and MIC activity of derivatives of compound 34 maintaining the biphenyl group with a piperazine modification.

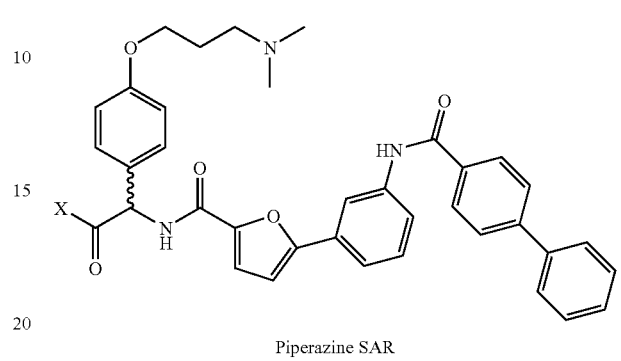

Piperazine SAR

| | X | translation IC50 (mM) | MIC, mM (E. coli) | MIC, mM (S. aureus) |
|---|---|---|---|---|
| 72 | (methoxycarbonyl piperazine) | >100 | >100 | >100 |

EXAMPLE 6

Several compounds were evaluated alone and with serum. It appears the biaryl compounds have significant serum protein binding.

TABLE 9

MIC activity of selected compounds alone, and with serum.

| MIC Activity with Serum compound | MIC, mM (E. coli) | | MIC, mM (S. aureus) | |
|---|---|---|---|---|
| | alone | +serum | alone | +serum |
| 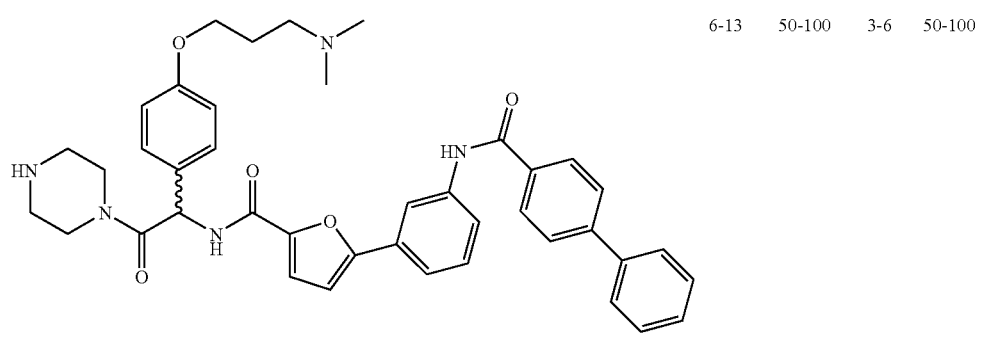 | 6-13 | 50-100 | 3-6 | 50-100 |

TABLE 9-continued

MIC activity of selected compounds alone, and with serum.

| MIC Activity with Serum compound | MIC, mM (*E. coli*) | | MIC, mM (*S. aureus*) | |
|---|---|---|---|---|
| | alone | +serum | alone | +serum |
| 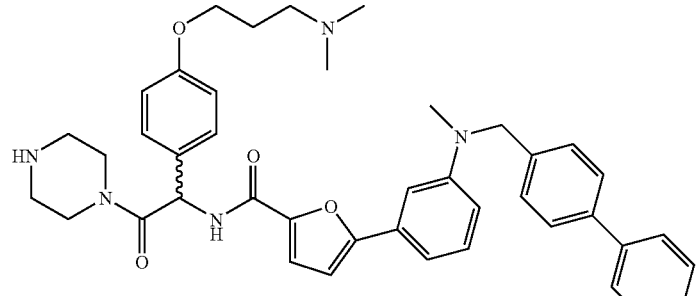 | 6-13 | >100 | 3-6 | 50-100 |
| 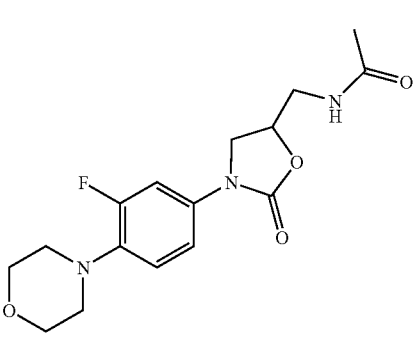 | 2-3 | 3-6 | <2-2 | 2-3 |

EXAMPLE 6

Additional compounds were made where the B-ring of the biphenyl group was substituted by a hydrogen bond donating group.

TABLE 10

Protein synthesis inhibitory activity and MIC activity of derivatives of compound 34 maintaining the biphenyl group substituted with an H-bond donor.

H-bond Donor on B-Ring

| Compound | translation IC50 (mM) | MIC, mM (*E. coli*) | MIC, mM (*S. aureus*) |
|---|---|---|---|
| 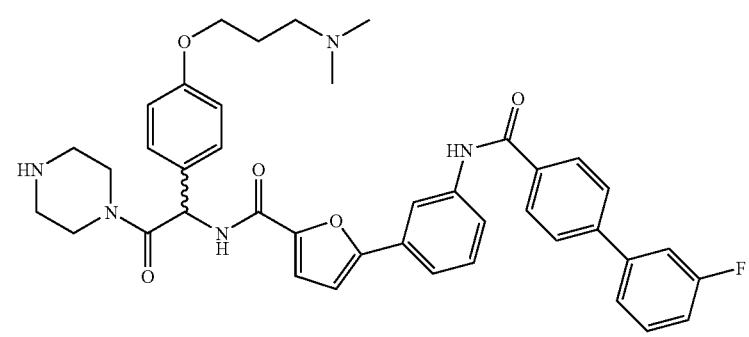 | 5 | 6-13 | 3-6 |

TABLE 10-continued

Protein synthesis inhibitory activity and MIC activity of derivatives of
compound 34 maintaining the biphenyl group substituted with an H-bond donor.
H-bond Donor on B-Ring

| Compound | translation IC50 (mM) | MIC, mM (E. coli) | MIC, mM (S. aureus) |
|---|---|---|---|
|  | 19 | >100 | 6-13 |

In some embodiments, the inventive compounds described and disclosed herein exhibit MIC activity against Gram-negative and Gram-positive bacterial strains, including a methicillin-resistant S. aureus strain.

EXAMPLE 7

Synthesis of Resins

Synthesis of Amine Resin

ArgoGel Rink-NH resin (Fmoc-deprotected) (Argonaut Technnologies, San Carlos), was treated with 4-iodo-3-nitrobenzoic acid (0.11M), collidine (2,3,5-trimethylpyridine) (0.25 M) and HATU (O-1-azabenzotriazol-1-yl)-N,N,N',N'-tetramethylamonium hexafluorophosphate) (0.11 M) in DMF, overnight at RT. The next day the resin was filtered and washed with DMF, DCM and MeOH.

Synthesis of Proline Resin (4)

ArgoGel Rink-NH resin (Fmoc-deprotected), was treated with Fmoc-Hyp(OtBu)-OH (0.11 M), collidine (0.25 M) and HATU (0.11 M) in DMF, overnight at RT. The next day the resin was filtered and washed with DMF, DCM and MeOH.

Synthesis of Piperazine Resin

A solution of carbonyldiimidazole (2 equiv, 1.14×10-2 mol) in DMF was added to ArgoGel Wang resin (5) (15 g, 0.38 mmol, 5.7×10-3 mmol). The reaction was left swirling over Ar, overnight. The next day the resin was washed with DMF (3×) and DCM (3×). The resin was dried in vacuo. A solution of piperazine (2.45 g, 5 equiv.) in DMF (50 mL) was then added to the resin and the reaction was left swirling overnight, over Ar. The next day the resin was washed with DCM (3×100 mL), DMF (3×100 mL) and MeOH (3×100 mL). The resin was then dried in vacuo. Resin (6) was then treated with 4-iodo-3-nitrobenzoic acid (0.11 M), collidine (0.25 M) and HATU (0.11 M) in DMF, overnight at RT. The next day the resin was filtered and washed with DMF, DCM and MeOH.

EXAMPLE 8

Biaryl Coupling

Using the IRORI combinatorial technology, resins described above were treated with tetrakistriphenylphosphine palladium (0) (0.017 M in dioxanes, 0.17 equiv.), 3-aminoboronic acid (0.6 M in EtOH, 6 equiv.), aqueous Na$_2$CO$_3$ (2 M, 13.3 equiv.), and anhydrous ethyleneglycol dimethyl ether (DME). The mixture was swirled and heated overnight at 70° C. under Ar. The next day the mixture was cooled to RT and filtered. The resin was washed with H$_2$O, DME-H$_2$O, DME, H$_2$O, 0.2 N HCl, 1:1 acetic acid-H$_2$O, and neat glacial acetic acid (3×). The resin was then dried in vacuo overnight over P$_2$O$_5$.

EXAMPLE 9

Acylation of Ring-B Amine

In a typical reaction, the carboxylic acid (0.11 M), HATU (0.11 M) in DMF were added to the reaction flask followed by collidine (0.25 M). For the reaction with 4-methoyxbenzyl isocyanate, a solution of 4-methoxyisocyanate (0.2 M) in DMF was added to the resin under Ar. The reaction was allowed to proceed overnight. The resin was filtered and the washed three times each with DMF, DCM, DMF and MeOH (3×). The resin was dried in vacuo overnight, over P$_2$O$_5$.

EXAMPLE 10

Attaching Heteroaryl A-Rings to Resins

Proline and piperazine resins prepared in example 7 are treated with 20% piperidine/DMF for 30 min. The resins are then washed with DMF, DCM and MeOH and dried under high vacuum over P$_2$O$_5$. The deprotected resins are reacted with 6-bromopicolinic acid, 5-bromofuroic acid, 5-bromonicotonic acid or 5-bromothiophene-2-carboxylic acid (shown) (0.11 M), HATU (0.11 M) and collidine (0.25 M) in DMF. The reactions are left stirring overnight, at RT. The next day the resins are filtered and washed with DMF, DCM and MeOH.

The techniques described above are generally useful in production of the biaryl compounds of related U.S. patent application Ser. No. 09/630,122. As such, techniques similar to those described above may be employed in the production of compounds described herein.

EXAMPLE 11

In Vitro Antibacterial Activity

Bacterial Strains. The Streptococcus pyogenes strains, Klebsiella pneumoniae, Escherichia coli, Staphylococcus aureus, Enterococcus faecalis used in the antibacterial activity studies ATCC 14289, 49399, 13883, 25922, 13709, 29212, respectively, are obtained from the American Type Culture Collection, Rockville, Md. The strain E. coli imp—is a mutant strain of wild type *E. coli* with increased outer membrane permeability and was grown in LB broth at 37°C. *S. pyogenes* strain is grown in Todd-Hewitt broth. *S. aureus* is grown in trypticase soy broth, *E. faecalis* in Todd-Hewitt broth, wild type *E. coli* and *K. pneumoniae*, in nutrient broth.

Determination of Minimum Inhibitory Concentrations (MICs). The assays were carried out in 150 L volume in duplicate in 96-well clear flat-bottom plates. The bacterial suspension from an overnight culture growth in appropriate medium was added to a solution of test compound in 4% DMSO in water. Final bacterial inoculum was approximately $10^5$-$10^6$ CFU/well. The percent growth of the bacteria in test wells relative to that observed for a well containing no compound was determined by measuring absorbance at 595 nm ($A_{595}$) after 24 h. The MIC was determined as a range of single compound where the complete inhibition of growth was observed at the higher concentration and cells were viable at the lower concentrations. Both ampicillin and tetracycline is used as antibiotic-positive controls in each screening assay for *S. pyogenes, E. coli* imp-, *E. coli, S. aureus, E. faecalis, K pneumoniae* and *P. vulgaris*. Ciprofloxacin is used as an antibiotic positive control in each screening assay for *P. aeruginosa*.

Mass-Spec Binding Assays.

Binding affinity of test compounds to a 58 nucleotide fragment of *E. coli* 23S ribosomal RNA (23S rRNA) was determined using electrospray ionization Fourier transform ion cyclotron resonance mass spectrometry (ESI-FTICR-MS). The structure of the 23S rRNA fragment and its preparation is described by Conn et al (Science, 1999, 284(5417):1171) and Hinck et al (J. Mol. Biol., 1997, 274(1):101) both incorporated herein by reference. The mass spec assay determined the exact chemical composition of ligands that bound to the target rRNA and determined relative or absolute dissociation ($K_D$) of ligands for the target. In the first step of the assay, a mixture of 23S rRNA target and test compound were moved from solution into the gas phase by electrospray ionization. The FT-ICR mass spectrometer served as a parallel set of "scales", simultaneously measuring the exact molecular masses of the small molecules that bound to the RNA with great accuracy. The mass measurement error for an RNA-ligand complex weighing 10 kDa equals the mass of an electron. At this level of mass accuracy, each compound in the mixture was "labeled" by its molecular formula and exact molecular mass. The assay was performed using standard 96-well plates with robotic liquid handlers to transfer mL amounts of sample into the mass spectrometer and was run with solutions containing magnesium and 200 mM ammonium acetate buffer to aid RNA folding, and 2% DMSO to dissolve potential ligands.

Animals and In Vivo studies. Male ICR mice are fed with autoclaved commercial food pellets and sterile water ad libitum. Animals are inoculated intraperitoneally with $8.0 \times 10^6$ CFU/0.5 mL/mouse of *K. pneumoniae* (ATCC 10031) in BHI containing 5% mucin. Ten animals each are randomly assigned to either control or treatment groups. Test compound (DMSO solution, 100 mg/kg, 33.3 mg/kg and 3.3 mg/kg) and gentamycin (3 mg/kg, included as a positive control) are both administered subcutaneously one hour after infection. Test compound is administered as a solution in DMSO (100%) and 50 μL/mouse while gentamycin is administered as an aqueous buffer solution (phosphate buffered saline (PBS), pH=7.4).

Coupled Bacterial Transcription/Translation Assay. The DNA template, pBestLuc™ (Promega), is a plasmid containing a reporter gene for firefly luciferase fused to a strong tac promoter and ribosome binding site. Messenger RNA from 1 μg pBestLuc was transcribed and translated in *E. coli* S30 bacterial extract in the presence or absence of test compound. Compounds were tested in a black 96 well microtiter plate with an assay volume of 35 μL. Each test well contained: 5 μL test compound, 13 μL S30 premix (Promega), 4 μL 10× complete amino acid mix (1 mM each), 5 μL *E. coli* S30 extract and 8 μL of 0.125 μg/mL pBestLuc™. The transcription/translation reaction was incubated for 35 minutes at 37° C. followed by detection of functional luciferase with the addition of 30 μL LucLite™ (Packard). Light output was quantitated on a Packard TopCount.

Amino Acid Misincorporation Assay. A mutant form of ubiquitin devoid of the amino acid tyrosine was produced in vitro in *E. coli* S-30 extracts in the presence of a tritiated tyrosine. Since ubiquitin has no tyrosine in the sequence, if tyrosine is used as the labeled amino acid, any incorporated counts above background is assumed to be due to the misincorporation of the tritiated amino acid. The labeled protein is captured via a ubiquitin antibody which is associated with anti-rabbit SPA beads. Altered ubiquitin molecules are not efficiently captured by the antibody. Compounds are tested in 96 well microtiter plate in an assay volume of 10 μL. Control experiments using the antibiotics, kanamycin, novabiocin, monensin, gentamicin, neomycin, tetracycline are run at 5 μM of each antibiotics. Test compounds are tested at 5 μM, 50 μM, and 500 μM.

Those skilled in the art will appreciate that numerous changes and modifications may be made to the preferred embodiments of the present invention, and that such changes and modifications may be made without departing from the spirit of the invention. It is, therefore, intended that the spirit and scope of the appended claims should not be limited to the description of the preferred embodiments contained herein, but, that the appended claims cover all such equivalent variations as fall within the true spirit and scope of the invention.

Each reference cited herein, including but not limited to patents, patent applications, patent publications, articles, and texts, are hereby incorporated by reference in its entirety.

We claim:

1. A compound having the formula:

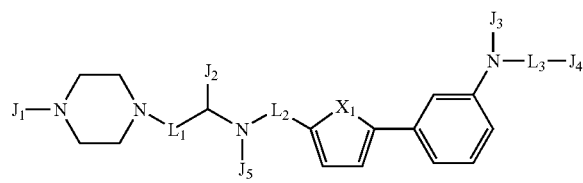

wherein
  $X_1$ is $CH_2$, O, S or NH;
  each $L_1$, $L_2$ and $L_3$ is, independently, $CR_1R_2$, C=O or S(=O)(=O);
  each $R_1$ and $R_2$ is, independently, H or $C_1$-$C_6$ alkyl;
  $J_1$ is H, $C_1$-$C_8$ alkyl; C(=O)O-alkyl or S(=O)(=O)-alkyl;
  $J_2$ is -p-$C_6H_4$—O—$(CH_2)_n$—$NR_3R_4$;
  each $R_3$ and $R_4$ is, independently, H or $C_1$-$C_6$ alkyl;
  each $J_3$ and $J_5$ is, independently, H or $C_1$-$C_6$ alkyl;
  $J_4$ has one of the formulas:

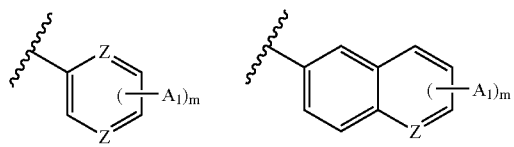

-continued

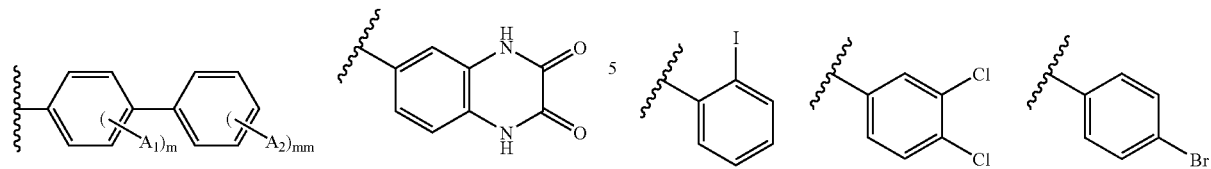

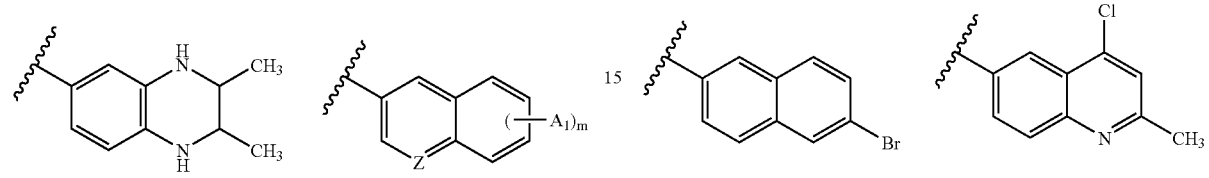

or

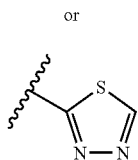

wherein:
    each Z is, independently, CH or N;
    each $A_1$ and $A_2$ is, independently, halogen, hydroxyl, amino, $C_1$-$C_6$ alkyl, $C_2$-$C_6$ alkenyl, $C_2$-$C_6$ alkynyl or alkoxy;
    n is from 1 about 6;
    m is 0, 1, 2, 3 or 4; and
    mm is 0, 1, 2, 3, 4 or 5.

2. The compound of claim 1 wherein $R_3$ and $R_4$ are each $C_1$-$C_6$ alkyl.

3. The compound of claim 2 wherein $R_3$ and $R_4$ are each $CH_3$.

4. A compound having the formula:

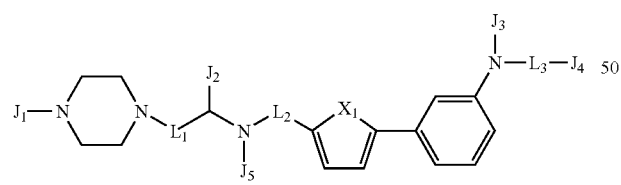

wherein
    $X_1$ is $CH_2$, O, S or NH;
    each $L_1$, $L_2$ and $L_3$ is, independently, $CR_1R_2$, C=O or S(=O)(=O);
    each $R_1$ and $R_2$ is, independently, H or $C_1$-$C_6$ alkyl;
    $J_1$ is H, $C_1$-$C_8$ alkyl; C(=O)O-alkyl or S(=O)(=O)-alkyl;
    $J_2$ is $-(CH_2)_n-NR_3R_4$ or $-p-C_6H_4-O-(CH_2)_n-{}_{NR3}R_4$;
    each $R_3$ and $R_4$ is, independently, H or $C_1$-$C_6$ alkyl;
    each $J_3$ and $J_5$ is, independently, H or $C_1$-$C_6$ alkyl;

$J_4$ has one of the formulas:

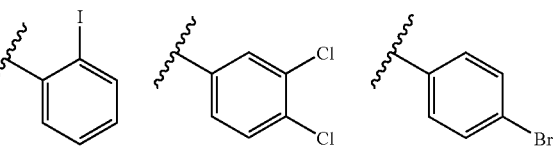

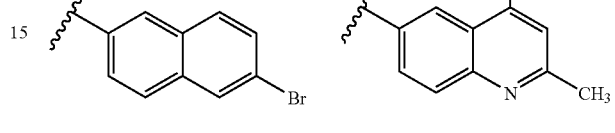

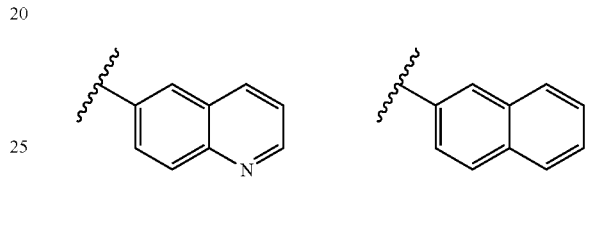

or

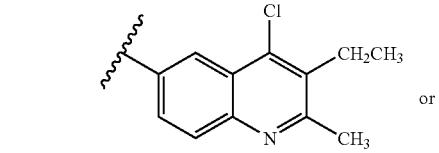

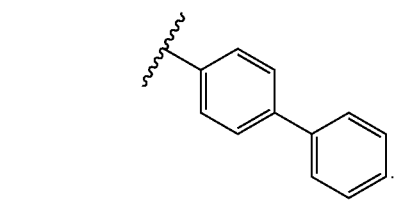

.

5. The compound of claim 4 wherein $L_1$ is C(=O).

6. A compound having the formula:

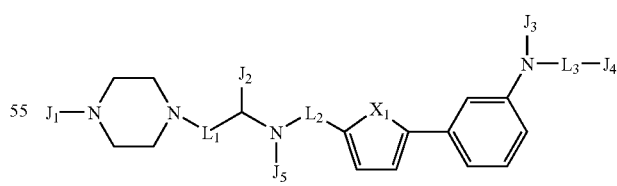

wherein
    $X_1$ is $CH_2$, O, S or NH;
    each $L_1$, $L_2$ and $L_3$ is, independently, $CH_2$, C=O or S(=O)(=O);
    $J_1$ is H, $C_1$-$C_8$ alkyl; C(=O)O-alkyl or S(=O)(=O)-alkyl;
    $J_2$ is -p-$C_6H_4$-O-$(CH_2)_n$-$NR_3R_4$;
    each $R_3$ and $R_4$ is, independently, H or $C_1$-$C_6$ alkyl;
    each $J_3$ and $J_5$ is, independently, H or $C_1$-$C_6$ alkyl;

$J_4$ has one of the formulas:

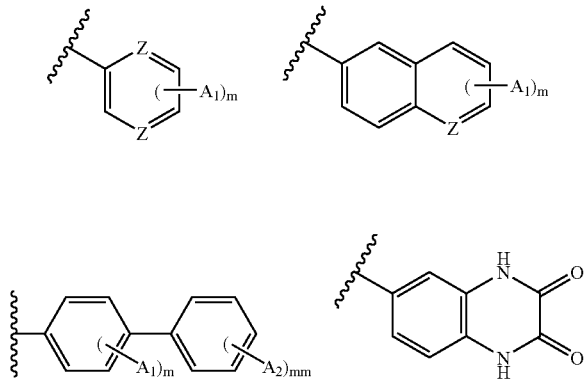

wherein:
  each Z is, independently, CH or N;
  each $A_1$ and $A_2$ is, independently, halogen, hydroxyl, amino, $C_1$-$C_6$ alkyl, $C_2$-$C_6$ alkenyl, $C_2$-$C_6$ alkynyl or alkoxy;
  n is from 1 to about 6;
  m is 0, 1, 2, 3 or 4; and
  mm is 0, 1, 2, 3, 4 or 5.

7. The compound of claim 6 wherein $R_3$ and $R_4$ are each $CH_3$.

8. A compound having the formula:

wherein
  $J_6$ is H or $C_1$-$C_8$ alkyl;
  $J_8$ has one of the formulas:

$J_7$ and $J_9$ are each, independently, H or $C_1$-$C_6$ alkyl.

9. The compound of claim 8 wherein $J_9$ is H.

10. The compound of claim 8 wherein $J_7$ and $J_9$ are each, independently, H.

* * * * *